(12) United States Patent
Schneider (10) Patent No.: US 11,877,796 B2
(45) Date of Patent: Jan. 23, 2024

(54) MATERIAL REMOVAL CATHETER HAVING AN EXPANDABLE DISTAL END

(71) Applicant: THE SPECTRANETICS CORPORATION, Colorado Springs, CO (US)

(72) Inventor: Blaine Schneider, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 512 days.

(21) Appl. No.: 14/700,550

(22) Filed: Apr. 30, 2015

(65) Prior Publication Data

US 2015/0342629 A1    Dec. 3, 2015

Related U.S. Application Data

(60) Provisional application No. 62/004,612, filed on May 29, 2014.

(51) Int. Cl.
| | | |
|---|---|---|
| A61B 18/24 | (2006.01) | |
| A61B 18/22 | (2006.01) | |
| A61B 18/20 | (2006.01) | |
| A61B 18/00 | (2006.01) | |

(52) U.S. Cl.
CPC .. *A61B 18/245* (2013.01); *A61B 2018/00577* (2013.01); *A61B 2018/00601* (2013.01); *A61B 2018/206* (2013.01); *A61B 2018/2211* (2013.01); *A61B 2218/007* (2013.01)

(58) Field of Classification Search
CPC ............ A61B 18/245; A61B 2218/007; A61B 2018/00601; A61B 2018/00577; A61B 2018/2255
See application file for complete search history.

(56) References Cited

U.S. PATENT DOCUMENTS

| | | | |
|---|---|---|---|
| 3,448,739 A | 6/1969 | Stark et al. | |
| 4,470,407 A | 9/1984 | Hussein | |
| 4,754,752 A | 7/1988 | Ginsburg et al. | |
| 4,781,681 A | 11/1988 | Sharrow et al. | |
| 4,790,310 A | 12/1988 | Ginsburg et al. | |
| 4,842,579 A | 6/1989 | Shiber | |

(Continued)

FOREIGN PATENT DOCUMENTS

| | | |
|---|---|---|
| DE | 198 42 113 A1 * | 3/2000 |
| EP | 0646360 B1 | 4/1995 |
| WO | 1991001690 A1 | 2/1991 |

OTHER PUBLICATIONS

Extended European Search Report for European Patent Application No. 08018059.9, dated Jan. 26, 2009, 6 pages.

(Continued)

*Primary Examiner* — Rene T Towa (57) ABSTRACT

Catheters for ablation and removal of occlusions from blood vessels are provided. Laser cutting systems and mechanical cutting systems are provided in catheter devices, the cutting systems operable to ablate, cut, dislodge, and otherwise remove occlusions within a blood vessel that may limit or prevent proper circulation. Catheters include expandable distal ends to facilitate, in some cases, relatively high bodily material removal rates compared to other devices.

22 Claims, 5 Drawing Sheets

(56) References Cited

U.S. PATENT DOCUMENTS

| | | | |
|---|---|---|---|
| 4,854,315 A | 8/1989 | Stack et al. |
| 4,862,887 A | 9/1989 | Weber et al. |
| 4,878,492 A | 11/1989 | Sinofsky et al. |
| 5,019,075 A | 5/1991 | Spears et al. |
| 5,053,033 A | 10/1991 | Clarke |
| 5,203,779 A | 4/1993 | Muller et al. |
| 5,290,278 A | 3/1994 | Anderson |
| 5,298,026 A | 3/1994 | Chang |
| 5,364,389 A | 11/1994 | Anderson |
| 5,377,683 A | 1/1995 | Barken |
| 5,395,361 A | 3/1995 | Fox et al. |
| 5,449,354 A | 9/1995 | Konwitz et al. |
| 5,451,221 A | 9/1995 | Cho et al. |
| 5,478,339 A | 12/1995 | Tadir et al. |
| 5,527,308 A | 6/1996 | Anderson et al. |
| 5,624,433 A | 4/1997 | Radisch et al. |
| 5,741,246 A | 4/1998 | Prescott |
| 5,772,972 A | 6/1998 | Hepburn et al. |
| 5,827,265 A | 10/1998 | Glinsky et al. |
| 6,106,515 A | 8/2000 | Winston et al. |
| 6,203,540 B1 | 3/2001 | Weber |
| 6,224,590 B1 | 5/2001 | Daikuzono |
| 6,485,485 B1 | 11/2002 | Winston et al. |
| 7,288,087 B2 | 10/2007 | Winston et al. |
| 8,182,474 B2 | 5/2012 | Winston et al. |
| 8,465,480 B2 | 6/2013 | Winston et al. |
| 9,254,175 B2 | 2/2016 | Winston et al. |
| 2002/0038125 A1* | 3/2002 | Hamilton | A61B 17/22031 606/115 |
| 2002/0173811 A1* | 11/2002 | Tu | A61B 17/22031 606/159 |
| 2011/0190579 A1* | 8/2011 | Ziarno | A61B 1/00016 600/109 |
| 2012/0197277 A1* | 8/2012 | Stinis | A61B 17/320758 606/159 |
| 2013/0225934 A1* | 8/2013 | Raybin | A61B 17/32056 600/214 |
| 2014/0052097 A1* | 2/2014 | Petersen | A61M 25/01 604/506 |
| 2016/0135893 A1 | 5/2016 | Winston et al. |

OTHER PUBLICATIONS

International Preliminary Examination Report for International Application No. PCT/US1999/017317, dated Oct. 13, 2000, 6 pages.

International Search Report for International Application No. PCT/US1999/017317, dated Oct. 27, 1999, 4 pages.

Masters, Barry R,; Early Development of Optical Low-Coherence Reflectometry and Some Recent Biomedical Applications, Journal of Biomedical Optics, Apr. 1999, pp. 236-247.

Supplementary European Search Report for European Patent No. 99937668.4 dated Aug. 27, 2007, 6 pages.

Supplementary Partial European Search Report for European Patent No. 99937668.4 dated May 30, 2007, 5 pages.

* cited by examiner

MATERIAL REMOVAL CATHETER HAVING AN EXPANDABLE DISTAL END

CROSS-REFERENCE TO RELATED APPLICATION

The present application claims the benefit of and priority to, under 35 U.S.C. § 119(e), U.S. Provisional Application Ser. No. 62/004,612, filed May 29, 2014, entitled MATERIAL REMOVAL CATHETER HAVING AN EXPANDABLE DISTAL END, which is hereby incorporated by reference in its entirety for all purposes.

FIELD

The present disclosure relates generally to medical devices, and, in particular, to expandable irrigation and aspiration catheters used in the containment and removal of material resulting from therapeutic treatment of occlusions within blood vessels.

BACKGROUND

Human blood vessels often become occluded or blocked by plaque, thrombi, other deposits, or emboli which reduce the blood carrying capacity of the vessel. Should the blockage occur at a critical place in the circulatory system, serious and permanent injury, and even death, can occur. To prevent this, some form of medical intervention is usually performed when significant occlusion is detected.

Balloon angioplasty and other transluminal medical treatments are well-known and have been proven efficacious in the treatment of stenotic lesions in blood vessels. The application of such medical procedures to certain blood vessels, however, has been limited, due to the risks associated with creation of emboli during the procedure. For example, angioplasty is not the currently preferred treatment for lesions in the carotid artery because of the possibility of dislodging plaque from the lesion, which can enter the various arterial vessels of the brain and cause permanent brain damage. Instead, surgical procedures such as carotid endarterectomy are currently used, wherein the artery is split open and the blockage removed, but these procedures present substantial risks of their own.

Other types of intervention for blocked vessels include atherectomy, deployment of stents, introduction of specific medication by infusion, and bypass surgery. Each of these methods are not without the risk of embolism caused by the dislodgement of the blocking material which then moves downstream. In addition, the size of the vessel may limit access to it.

There is also a need to efficiently remove occlusions from a patient without excess undesired removal of native blood and tissue within the system. Constant flow suction or vacuum pressure is effective at removing freed or dislodged occlusions, but typically remove unnecessary amounts of blood in the process. Thus, there is a need for a system to effectively contain and remove such emboli without undesired consequences, such as excess removal of blood and tissue from the vessel.

Vessels as small as 3 mm in diameter are quite commonly found in the coronary arteries, and even certain saphenous vein graph bypass vessels can also be as small as 3 mm or 4 mm; although some can be as large as 7 mm. Carotid arteries can also be as small as 4 mm in diameter; although, again, others may be larger. Nevertheless, a successful emboli removal system must be effective within extremely small working areas.

Another obstacle is the wide variety in emboli dimensions. Although definitive studies are not available, it is believed that emboli may have approximate diameters ranging anywhere from tens of micrometers to a few hundred micrometers. More specifically, emboli that may be dangerous to the patient have diameters greater than 100 micrometers. Thus, an effective emboli removal system must be able to accommodate relatively large embolic particles and, at the same time, fit within relatively small vessels.

Another difficulty that must be overcome is the limited amount of time available to perform the emboli removal procedure. That is, in order to contain the emboli produced as a result of intravascular therapy, the vessel must be occluded, meaning that no blood perfuses through the vessel to the end organs. Although certain perfusion systems may exist or may be developed which would occlude emboli while permitting the substantial flow of blood, at present, the emboli may be contained only with a complete occlusion as to both blood flow and emboli escapement. Again depending upon the end organ, the complete procedure, including time for the therapeutic treatment as well as exchanges of angioplastic balloons, stents, and the like, must be completed within a short time. Thus, it may be difficult to include time for emboli removal as well. This is particularly true in the larger size vessels discussed above wherein a larger volume results in additional time required for emboli evacuation.

Similarly, the time needed to perform the above removal procedures is typically increased by the need to conduct multiple passes with the material removal device, especially for larger vessels. Multiple passes are typically required due to the relatively small size of material removal devices. That is, clinicians typically prefer to use relatively small devices (e.g., 6F or smaller) because such devices reduce potential bleeding and infection issues at the point of insertion compared to larger devices.

Additionally, there has been an unmet need to provide a catheter that is adept at removing harder material, such as calcium (e.g. harder than thrombus and plaque). Cutting and removal of such harder materials generally requires additional procedure time and increased risks.

Moreover, it is important to physicians that an emboli containment and removal system be easy to use, and compatible with present therapeutic devices and methods.

SUMMARY

These and other needs are addressed by the various aspects, embodiments, and configurations of the present disclosure.

In some embodiments, a catheter system for cutting bodily material of a subject includes a catheter having a wall. The wall includes a distal end carrying a cutting instrument adapted to cut bodily material of the subject. The distal end is reconfigurable from a collapsed configuration to an expanded configuration, and the wall further includes an orifice disposed at the distal end. The orifice is in fluid communication with a lumen extending proximally from the distal end. The lumen is adapted to receive cut bodily material. The catheter system further includes a release mechanism coupled to the catheter. The release mechanism is actuatable to reconfigure the distal end from the collapsed configuration to the expanded configuration.

In some embodiments, a catheter system for cutting bodily material of a subject includes a catheter having a wall. The wall includes a distal end carrying a cutting instrument adapted to cut bodily material of the subject. The distal end is reconfigurable from a collapsed configuration to an expanded configuration. The wall further includes an orifice disposed at the distal end, and the orifice is in fluid communication with a lumen extending proximally from the distal end. The lumen is adapted to receive cut bodily material. A sheath is translatably carried by the catheter. The sheath is translatable from a first position relative to the catheter to a second position relative to the catheter. In the first position the sheath urges the distal end toward the collapsed configuration, and in the second position the sheath permits the distal end to occupy the expanded configuration.

In some embodiments, a catheter system for cutting bodily material of a subject includes a catheter having a wall. The wall includes a distal end carrying a cutting instrument adapted to cut bodily material of the subject. The distal end being reconfigurable from a collapsed configuration to an expanded configuration. The wall further includes an orifice disposed at the distal end, and the orifice is in fluid communication with a lumen extending proximally from the distal end. The lumen is adapted to receive cut bodily material. A cover is carried by the catheter. The cover surrounds the distal end to hold the distal end in the collapsed configuration. The cover is proximally slidable along the catheter to expose the distal end and permit the distal end to occupy the expanded configuration.

In various embodiments, the device of the present disclosure may not only be used for dissecting, coring and aspirating plug-type portions of lesion material, but the device or embodiments of the device of the present disclosure may be used to perform bulk ablation. Bulk ablation generally encompasses the use of catheter having a full face of laser emitters at its distal end, and all of the lesion material contacted by the energy transmitted by the laser emitters is ablated, in comparison to ablating the lesion with a circular or helical arrangement of lasers and coring the tissue. Depending upon the size and type of lesion, the bulk ablation technique may potentially increase the efficiency of the system and removal of debris. Such a technique may be used by a user/physician based on the specific removal needs and may comprise, for example, inserting an additional laser catheter through a central lumen to provide a substantially flat laser ablation distal end of the catheter.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "computer-readable medium" as used herein refers to any storage and/or transmission medium that participate in providing instructions to a processor for execution. Such a medium is commonly tangible and non-transient/non-transitory and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is typically equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The terms "determine", "calculate" and "compute," and variations thereof, as used herein, are used interchangeably and include any type of methodology, process, mathematical operation or technique.

A "laser emitter" refers to an end portion of a fiber or an optical component that emits laser light from a distal end of the catheter towards a desired target, which is typically tissue.

An optical fiber (or laser active fibre) is a flexible, transparent fiber made of an optically transmissive material, such as glass (silica) or plastic, that functions as a waveguide, or "light pipe", to transmit light between the two ends of the fiber.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Although a large portion of this disclosure includes a discussion of laser catheters (or catheters having a combination of laser emitters and mechanical cutting instruments at the distal end) used in conjunction with an aspiration system, catheters having mechanical cutting instruments may also be used. Laser catheters typically transmit laser energy through optical fibers housed in a relatively flexible tubular catheter inserted into a body lumen, such as a blood vessel, ureter, fallopian tube, cerebral artery and the like to remove obstructions in the lumen. Catheters used for laser angioplasty and other procedures may have a central passageway or tube which receives a guide wire inserted into the body lumen (e.g., vascular system) prior to catheter introduction. The guide wire facilitates the advancement and placement of the catheter to the selected portion(s) of the body lumen for laser ablation of tissue.

Examples of laser catheters or laser sheath are sold by the Spectranetics Corporation under the tradenames ELCA™ and Turbo Elite™ (each of which is used for coronary intervention or catheterization such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler, which connects to a laser system or generator. One such example of a laser system is the CVX-300 Excimer Laser System, which is also sold by the Spectranetics Corporation.

Figure 1:
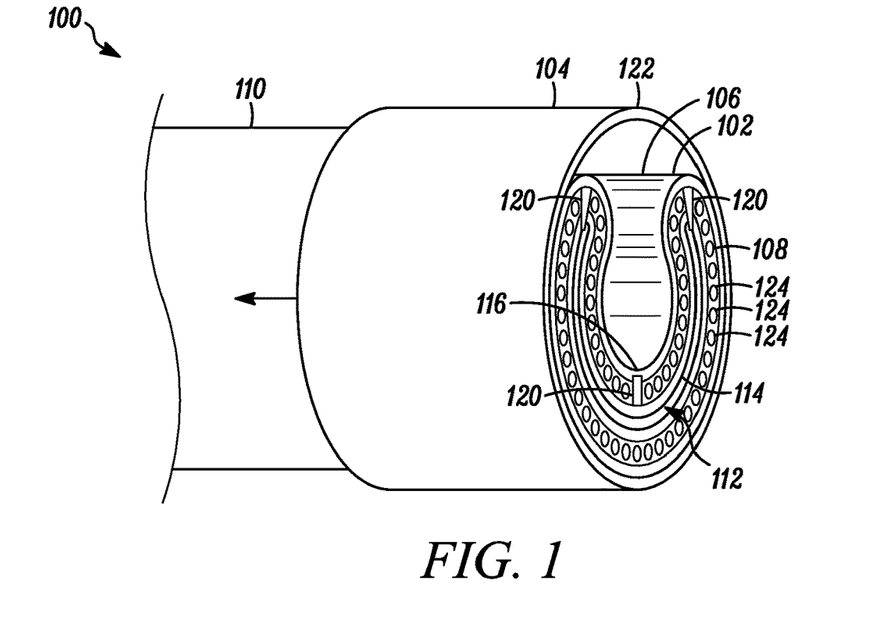
FIG. 1 is a side perspective view of a distal end of a catheter system according to one embodiment of the present disclosure; the distal end is illustrated in a collapsed configuration.
Figure 2:
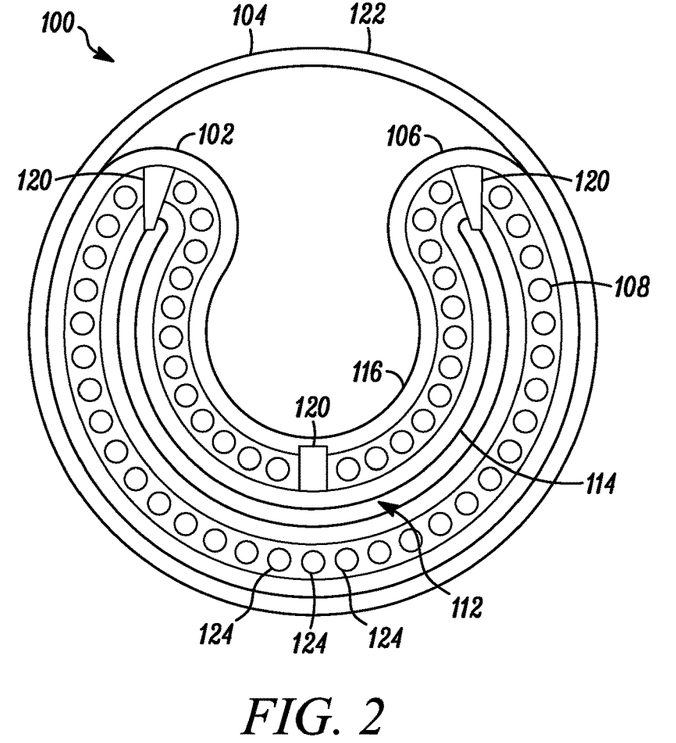
FIG. 2 is an end view of the catheter system of FIG. 1.
Figure 3:
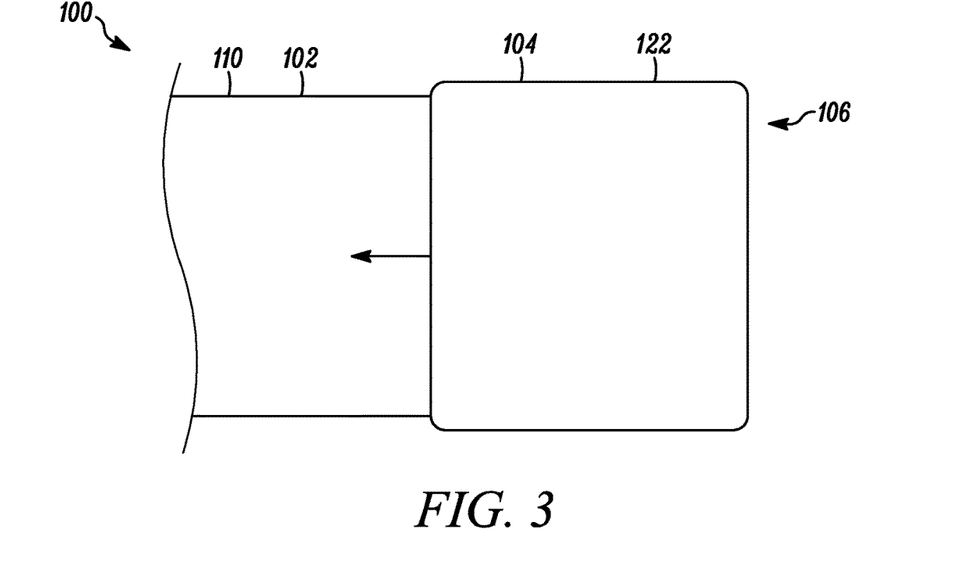
FIG. 3 is a side view of the catheter system of FIG. 1.
Figure 4:
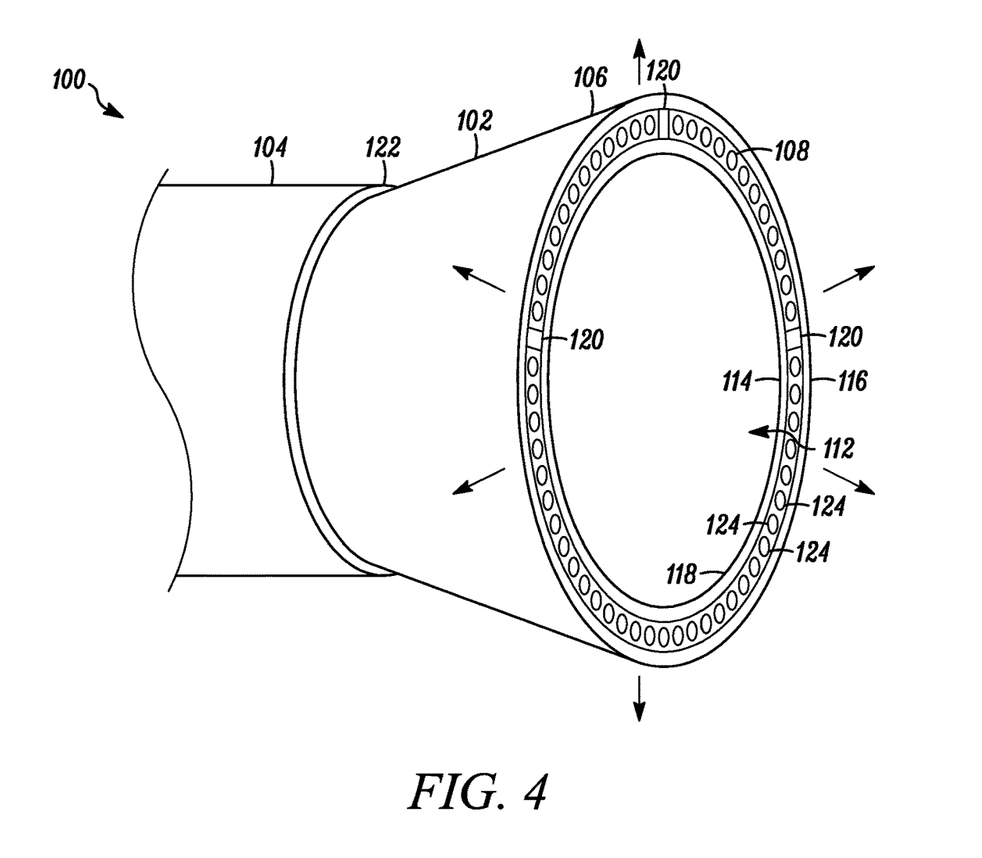
FIG. 4 is a side perspective view of the catheter system of FIG. 1; the distal end is illustrated in an expanded configuration.
Figure 5:
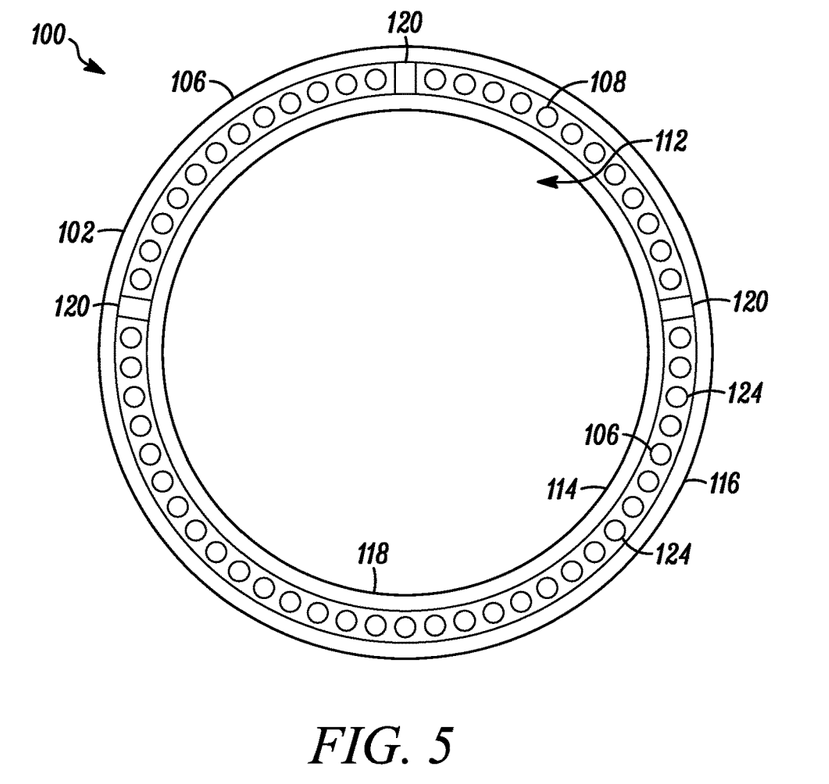
FIG. 5 is an end view of the catheter system of FIG. 4;'
Figure 6:
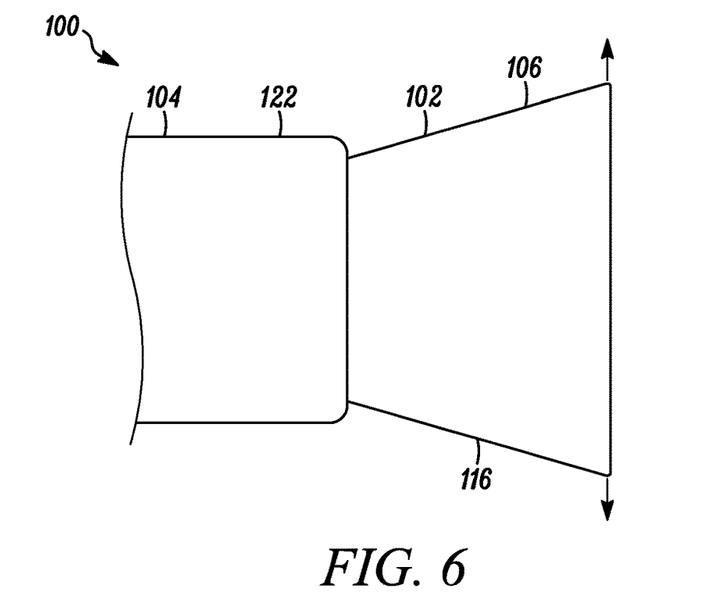
FIG. 6 is a side view of the catheter system of FIG. 4.

Referring now to FIGS. 1-6, a catheter system 100 for atherectomy procedures in accordance with one embodiment of the present disclosure is shown. The catheter system 100 generally includes a catheter 102 and a release mechanism 104. A distal end 106 of the catheter 102 includes a first cutting instrument 108 that is adapted to cut (that is, mechanically cut, laser ablate, or the like) bodily material (for example, scar tissue, plaque build-up, calcium deposits, or the like). The distal end 106 is reconfigurable from a collapsed configuration (as depicted in FIGS. 1-3) to an expanded configuration (as depicted in FIGS. 4-6). In the collapsed configuration, the distal end 106 defines a first, relatively small cross-sectional area. For example, referring to FIG. 1 and FIG. 2, when the distal end 106 of the catheter 102 is in the collapsed configuration, the distal end 106 comprises two folds, which create two "U"-shaped folded portions that are adjacent one another (in a horseshoe shape) at the distal end 106 of the catheter 102. In the expanded configuration, the distal end 106 defines a second, relatively large cross-sectional area. The first cross-sectional area is less than the second cross-sectional area. In addition, the first cross-sectional area may have approximately the same cross-sectional area as an adjacent portion 110 of the catheter 102 (for example, less than about 6F). As such, the distal end 106 may occupy the collapsed configuration when the catheter 102 is inserted into a subject's vasculature to reduce bleeding and infection risks. The second cross-sectional area may be significantly larger than cross-sectional area of the adjacent portion 110 of the catheter 102. As such, when the distal end 106 is appropriately positioned within the subject's vasculature, the distal end 106 may be reconfigured, via the release mechanism 104, to occupy the expanded configuration. The catheter system 100 may have a relatively high tissue removal rate due to the relatively large cross-sectional area of the distal end 106 in the expanded configuration. Stated another way, the catheter system 100 may remove a relatively large amount of bodily material from the subject in a single pass compared to other devices.

The catheter 102 may include a lumen 112. Cut bodily material may be drawn through the lumen 112 and removed from the subject via a vacuum pump (not shown). If the catheter 102 includes a lumen 112, a clinician may slide the catheter 102 over a guidewire (not shown) extending through the lumen 112. It may, however, be preferable for the catheter 102 to have a separate guidewire lumen (not shown) located between an inner wall 114 and an outer wall 116 of the catheter 102. Incorporation of such a guidewire lumen is generally known to one of ordinary skill in the art, and all guidewire lumens within the knowledge of one skilled in the art are considered within the scope of this disclosure.

The inner wall 114 and the outer wall 116 may comprise any of various flexible materials, such as polymers, metals, combinations thereof, and the like. The inner wall 114 and the outer wall 116 resist user-applied forces such as torque, tension, and compression. The inner wall 114 and the outer wall 116 may provide a funnel shape in the expanded configuration of the distal end 106. Such a funnel shape may taper inwardly proceeding proximally away from the distal end 106. Such a funnel shape has a distal orifice 118 in fluid communication with the lumen 112.

The inner wall 114 and the outer wall 116 carry one or more flexible components 120 that facilitate reconfiguring the distal end from the collapsed configuration to the expanded configuration. If the catheter 102 includes multiple flexible components 120, the flexible components 120 may be disposed at multiple locations about the distal end 106. For example, referring to FIG. 1 and FIG. 2, the flexible components 120 may be disposed adjacent the folds and/or in the wall within the folded portion between the folds. The flexible component(s) 120 may be more flexible than the inner wall 114 and outer wall 116. In such embodiments, the flexible component(s) 120 may provide preferential areas at which the distal end 106 folds when reconfigured from the expanded configuration to the collapsed configuration. The flexible component(s) 120 may store energy in order to urge the distal end 106 toward the expanded configuration. The flexible component(s) 120 may comprise any of various flexible materials, such as elastic polymers, shape memory metals, or the like.

The release mechanism 104 is actuatable to reconfigure the distal end 106 from the collapsed configuration to the expanded configuration and, in some embodiments, from the expanded configuration to the collapsed configuration. In the illustrated embodiment, the release mechanism 104 is a translatable sheath 122, sleeve, or cover. In a first position, the sheath 122 encloses the catheter 102 to hold the distal end 106 in the collapsed configuration. The sheath 122 may be translated proximally (for example, by sliding the sheath 122 along the outer wall 116) to move to a second position. In the second position, the sheath 122 is disposed apart from the distal end 106 to permit the distal end 106 to reconfigure to the expanded configuration (for example, by permitting the flexible component(s) 120 to urge the distal end 106 to the expanded configuration).

The sheath 122 may comprise any of various flexible, semi-flexible, semi-rigid or rigid materials, such as relatively-rigid plastics, metals, or the like. In some embodiments, the sheath 122 may be translated proximally via a pullwire (not shown). In some embodiments, the sheath 122 may be an elongated component that includes a graspable proximal portion (not shown). The proximal portion may be pulled by the clinician to translate the sheath 122 from the first configuration to the second configuration (i.e., to reconfigure the distal end 106 from the collapsed configuration to the expanded configuration). In some embodiments, the proximal portion may be pushed by the clinician to translate the sheath 122 from the second configuration to the first configuration (i.e., to reconfigure the distal end 106 from the expanded configuration to the collapsed configuration). In such embodiments, a distal portion of the sheath 122 (i.e., the portion that holds the distal end 106 of the catheter 102 in the collapsed position) may comprise a relatively rigid material, and the remainder of the sheath 122 may comprise a relatively flexible material to facilitate positioning the catheter system 100 in the subject's vasculature.

The first cutting instrument 108 is adapted to cut (that is, mechanically cut, laser ablate, or the like) bodily material (for example, scar tissue, plaque build-up, calcium deposits, or the like). In the illustrated embodiment, the cutting instrument 108 is provided as a plurality of optical fibers 124 that act as laser emitters. The optical fibers 124 are adapted to receive laser energy from a laser source (not shown), such as a Spectranetics® CVX-300 Excimer Laser System, and transmit the laser energy for cutting bodily material. In some embodiments, the optical fibers 124 comprise 100 µm fibers provided in a circular arrangement. In some embodiments, the optical fibers 124 comprise 100 µm fibers provided in an arrangement of multiple concentric circles. The optical fibers 124 may be protected from damage and oriented correctly at the distal end 106 of the catheter 102 for laser ablation. In various embodiments, approximately fifty to one hundred optical fibers 124 capable of transmitting laser energy of approximately 130 µm wavelength are provided. It will be recognized, however, that the present disclosure is not limited to a particular number or arrangement of optical fibers. Various alternative arrangements and quantities of optical fibers are contemplated as within the scope and spirit of the present disclosure. In alternative embodiments, any combination of optical fiber size can be utilized, including 61/100/130 µm fibers, either in substantially circular or ovoid cross-section.

Figure 7:
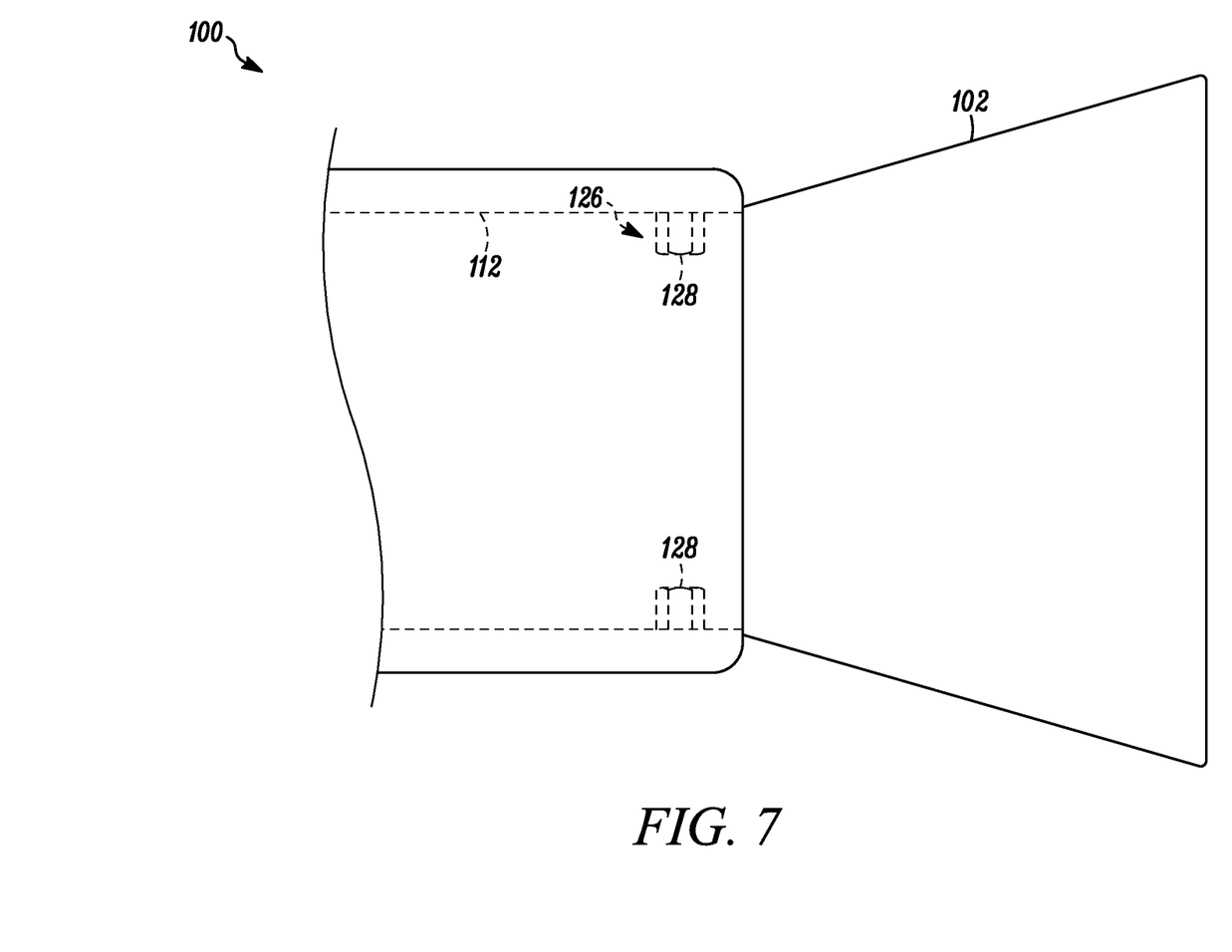
FIG. 7 is a side view of a distal end of a catheter system according to one embodiment of the present disclosure; the distal end is illustrated in an expanded configuration.
Figure 8:
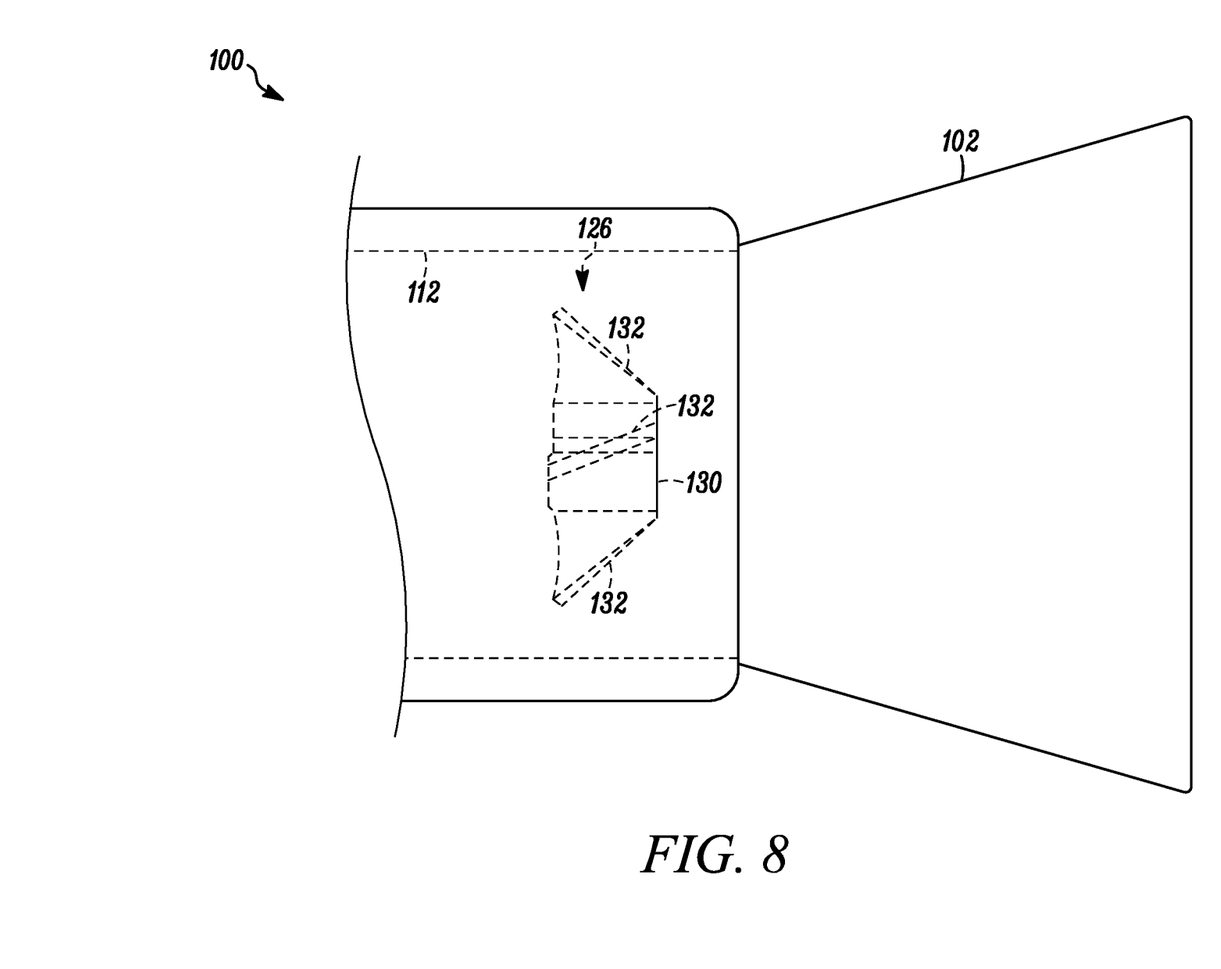
FIG. 8 is a side view of a distal end of a catheter system according to one embodiment of the present disclosure; the distal end is illustrated in an expanded configuration.

Referring to FIGS. 7 and 8, in some embodiments the catheter 102 may carry a second cutting instrument 126 to inhibit clogging within the lumen 112. In some embodiments, the second cutting instrument 126 may be disposed within the adjacent portion 110 of the catheter 102.

In some embodiments and as illustrated in FIG. 7, the second cutting instrument 126 may be a plurality of optical fibers 128 that act as laser emitters. The optical fibers 128 are adapted to receive laser energy from a laser source (not shown), such as a Spectranetics® CVX-300 Excimer Laser System, and transmit the laser energy for cutting bodily material. In some embodiments, the optical fibers 128 receive laser energy from the same laser source as the optical fibers 124 described above. The number and type of optical fibers 128 may be as described above or may take other appropriate forms.

In some embodiments and as illustrated in FIG. 8, the second cutting instrument 126 may be a rotatable cutting blade 130 that includes multiple cutting vanes 132. The cutting blade 130 may be constructed of, for example, stainless steels, abrasive materials, diamond tip, or the like.

The second cutting instrument 126 may take various other appropriate forms.

A number of variations and modifications of the disclosure can be used. It would be possible to provide for some features of the disclosure without providing others. Furthermore, embodiments of systems and methods according to the present disclosure may include and/or be used in conjunction with any of the systems, devices, structures, and/or methods described in U.S. patent application Ser. Nos. 13/800,651, 13/800,675, 13/800,700, and/or 13/800,728, all of which were filed on Mar. 13, 2013, the disclosures of which are hereby incorporated by reference in their entireties.

As another example, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a non-transient/non-transitory storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An intravascular therapy catheter system for cutting a blood vessel occlusion of a subject, the catheter system comprising:

a catheter configured for insertion into a blood vessel of the subject, the catheter having a wall, the wall comprising a distal end carrying a cutting instrument adapted to cut material of an occlusion in the blood vessel of the subject, the distal end being reconfigurable from a collapsed configuration to an expanded configuration, the wall further comprising at least two flexible components, wherein the at least two flexible components have a first flexibility that is different than a flexibility for another portion of the wall, wherein the wall comprises two folds in the collapsed configuration, wherein the at least two flexible components are within the two folds, respectively, wherein the two folds create two folded portions, wherein a first of the two folded portions comprises a first U shape having a concave surface, wherein the second of the two folded portions comprises a second U shape having a convex surface, the second U shape coupled to the first U shape at the two folds, the wall further comprising a U shaped orifice disposed at the distal end between the first U shape and the second U shape, the orifice being in fluid communication with a lumen extending proximally from the distal end, the lumen being adapted to receive the cut material of the occlusion in the blood vessel of the subject; and a release mechanism coupled to the catheter, the release mechanism being actuatable to reconfigure the distal end from the collapsed configuration to the expanded configuration;

wherein, in the collapsed configuration, the second of the two folded portions is spaced from an inner surface of the release mechanism by the first of the two folded portions, and in the expanded configuration, the second of the two folded portions contact the inner surface of the release mechanism.

2. The catheter system of claim 1, wherein the distal end comprises a funnel shape in the expanded configuration.

3. The catheter system of claim 2, further comprising a vacuum pump in fluid communication with the lumen and adapted to displace cut material of the occlusion in the blood vessel of the subject through the lumen.

4. The catheter system of claim 3, wherein the cutting instrument is a first cutting instrument, and the catheter further comprises a second cutting instrument disposed within the lumen, the second cutting instrument being adapted to cut material of the occlusion in the blood vessel of the subject within the lumen.

5. The catheter system of claim 1, wherein the release mechanism comprises a sleeve carried by the catheter, the sleeve being actuatable from a first position relative to the catheter to a second position relative to the catheter, in the first position the sleeve urging the distal end toward the collapsed configuration, and in the second position the sleeve permitting the distal end to occupy the expanded configuration.

6. The catheter system of claim 1, wherein the wall comprises a third flexible component.

7. An intravascular catheter system for cutting a blood vessel occlusion of a subject, the catheter system comprising:

A catheter configured for insertion into a blood vessel of the subject, the catheter having a wall, the wall comprising a distal end carrying a cutting instrument adapted to cut material of the occlusion in the blood vessel of the subject, the distal end being reconfigurable from a collapsed configuration to an expanded configuration, the wall further comprising at least two flexible components, wherein the at least two flexible components have a first flexibility that is different than a flexibility for another portion of the wall, wherein the wall comprises two folds in the collapsed configuration, wherein the at least two flexible components are within the two folds, respectively, wherein the two folds create two folded portions, wherein a first of the two folded portions comprises a first U shape having a concave surface, wherein the second of the two folded portions comprises a second U shape having a convex surface, the second U shape coupled to the first U shape at the two folds, the wall further comprising a U shaped orifice disposed at the distal end between the first U shape and the second U shape, the orifice being in fluid communication with a lumen extending proximally from the distal end, the lumen being adapted to receive the cut material of the occlusion in the blood vessel of the subject; and a sheath translatably carried by the catheter, the sheath being translatable from a first position relative to the catheter to a second position relative to the catheter, in the first position the sheath urging the distal end toward the collapsed configuration, and in the second position the sheath permitting the distal end to occupy the expanded configuration;

wherein, in the collapsed configuration, the second of the two folded portions is spaced from an inner surface of the sheath, and in the expanded configuration, the second of the two folded portions contact the inner surface of the sheath.

8. The catheter system of claim 7, wherein in the first position the sheath encloses the distal end to urge the distal end toward the collapsed configuration, and in the second position the sheath is disposed proximally from the distal end to permit the distal end to occupy the expanded configuration.

9. The catheter system of claim 7, wherein the at least two flexible components urge the distal end toward the expanded configuration.

10. The catheter system of claim 9, wherein the at least two flexible components reconfigure the distal end from the collapsed configuration to the expanded configuration when the sheath occupies the second position.

11. The catheter system of claim 9, wherein the cutting instrument comprises a plurality of optical fibers disposed apart from the at least two flexible components, the plurality of optical fibers being adapted to act as laser emitters.

12. The catheter system of claim 7, wherein the cutting instrument comprises a plurality of optical fibers adapted to act as laser emitters.

13. The catheter system of claim 7, wherein the cutting instrument is a first cutting instrument, and the catheter further comprises a second cutting instrument disposed within the lumen, the second cutting instrument being adapted to cut material of the occlusion in the blood vessel of the subject within the lumen.

14. The catheter system of claim 7, further comprising a vacuum pump in fluid communication with the lumen and adapted to displace the cut material of the occlusion in the blood vessel of the subject through the lumen.

15. The catheter system of claim 7, wherein the wall comprises a third flexible component.

16. An intravascular therapy catheter system for cutting a blood vessel occlusion of a subject, the catheter system comprising:

a catheter having a wall, the wall comprising a distal end carrying a cutting instrument adapted to cut material of the occlusion in the blood vessel of the subject, the distal end being reconfigurable from a collapsed configuration to an expanded configuration, the wall further comprising at least two flexible components, wherein the at least two flexible components have a first flexibility that is different than a flexibility for another portion of the wall, wherein the wall comprises two folds in the collapsed configuration, wherein the at least two flexible components are within the two folds, respectively, wherein the two folds create two folded portions, wherein a first of the two folded portions comprises a first U shape having a concave surface, wherein the second of the two folded portions comprises a second U shape having a convex surface, the second U shape coupled to the first U shape at the two folds, the wall further comprising a U shaped orifice disposed at the distal end between the first U shape and the second U shape, the orifice being in fluid communication with a lumen extending proximally from the distal end, the lumen being adapted to receive the cut material of the occlusion in the blood vessel of the subject; and a cover carried by the catheter, the cover surrounding the distal end to hold the distal end in the collapsed configuration, and the cover being proximally slidable along the catheter to expose the distal end and permit the distal end to occupy the expanded configuration;

wherein, in the collapsed configuration, the second of the two folded portions is spaced from an inner surface of the cover.

17. The catheter system of claim 16, wherein the at least two flexible components urge the distal end toward the expanded configuration.

18. The catheter system of claim 17, wherein the at least two flexible components reconfigure the distal end from the collapsed configuration to the expanded configuration when the distal end is exposed from the cover.

19. The catheter system of claim 16, wherein the cutting instrument comprises a plurality of optical fibers adapted to act as laser emitters.

20. The catheter system of claim 16, wherein the cutting instrument is a first cutting instrument, and the catheter further comprises a second cutting instrument disposed within the lumen, the second cutting instrument being adapted to cut material of the occlusion in the blood vessel of the subject within the lumen.

21. The catheter system of claim 16, wherein the cutting instrument is a mechanical cutting instrument.

22. The catheter system of claim 16, wherein the wall comprises a third flexible component.

* * * * *